United States Patent [19]

Harjunmaa

[11] Patent Number: 4,555,178
[45] Date of Patent: Nov. 26, 1985

[54] METHOD FOR THE MEASUREMENT OF THE DIFFERENCE IN THE OPTICAL PROPERTIES DEPENDENT ON THE LIGHT DIRECTION OF TWO SAMPLES

[75] Inventor: Hannu Harjunmaa, Espoo, Finland

[73] Assignee: Labsystems Oy, Helsinki, Finland

[21] Appl. No.: 579,887

[22] PCT Filed: Jun. 21, 1983

[86] PCT No.: PCT/FI83/00050
§ 371 Date: Feb. 2, 1984
§ 102(e) Date: Feb. 2, 1984

[87] PCT Pub. No.: WO84/00213
PCT Pub. Date: Jan. 19, 1984

[30] Foreign Application Priority Data

Jun. 29, 1982 [FI] Finland .................................. 822306

[51] Int. Cl.⁴ ............................................ G01N 21/47
[52] U.S. Cl. .................................... 356/339; 356/341;
356/371; 356/434; 356/442; 356/446; 356/447
[58] Field of Search ................. 356/73, 408, 339, 341,
356/433, 434, 442, 445–448, 371

[56] References Cited

U.S. PATENT DOCUMENTS 3,892,492 7/1975 Eichenberger .................. 356/447 X

FOREIGN PATENT DOCUMENTS 690372 10/1979 U.S.S.R. ............................. 356/339

Primary Examiner—F. L. Evans
Attorney, Agent, or Firm—Hopgood, Calimafde, Kalil, Blaustein & Judlowe

[57] ABSTRACT

Method for the measurement of the difference in the optical properties dependent on the light direction of two samples (1,2), in which method one or several sources of light (3 to 6) as well as one light detector (7) are used. According to the invention, both of the samples (1, 2) are illuminated simultaneously and from both samples (1, 2) the light is passed simultaneously to the light detector (7). The lights to be measured from the samples (1, 2) have different directions in relation to the sample. The directions of the lights to be measured from the samples (1, 2) are alternated with each other at an appropriate frequency, such as a frequency within the range of 1 c/s to 10,000 c/s. The AC signal given by the light detector (7) is used as a measure of the difference in some optical property dependent on the direction of light between the samples, such as, e.g., as a measure of the turbidity of a solid, liquid or gaseous sample, or as a measure of the reflectivity or transparency of a face or film sample as a function of the direction of light.

3 Claims, 2 Drawing Figures

METHOD FOR THE MEASUREMENT OF THE DIFFERENCE IN THE OPTICAL PROPERTIES DEPENDENT ON THE LIGHT DIRECTION OF TWO SAMPLES

The present invention is concerned with a method for the measurement of the difference in the optical properties dependent on the light direction of two samples, in which method one or several sources of light as well as one light detector are used. By means of the method in accordance with the invention, the difference is obtained by means of one measurement.

The samples for which the method in accordance with the invention is suitable may be solid, liquid or gaseous volume samples, or faces that reflect light, or films transparent to light.

Figure 1:
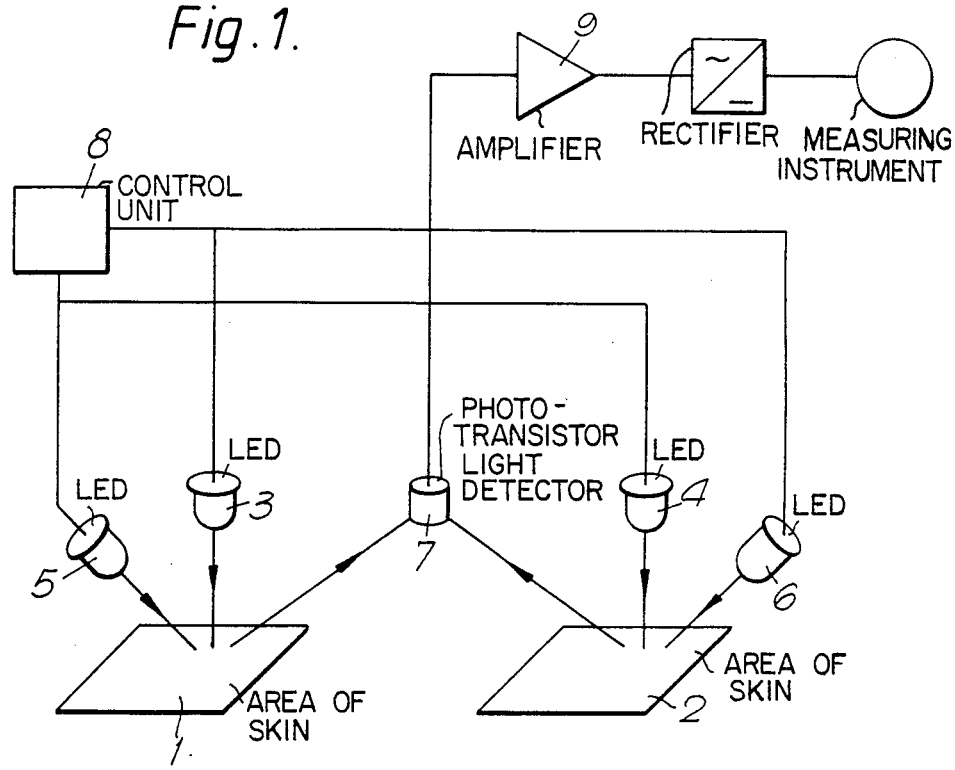
Figure 2:
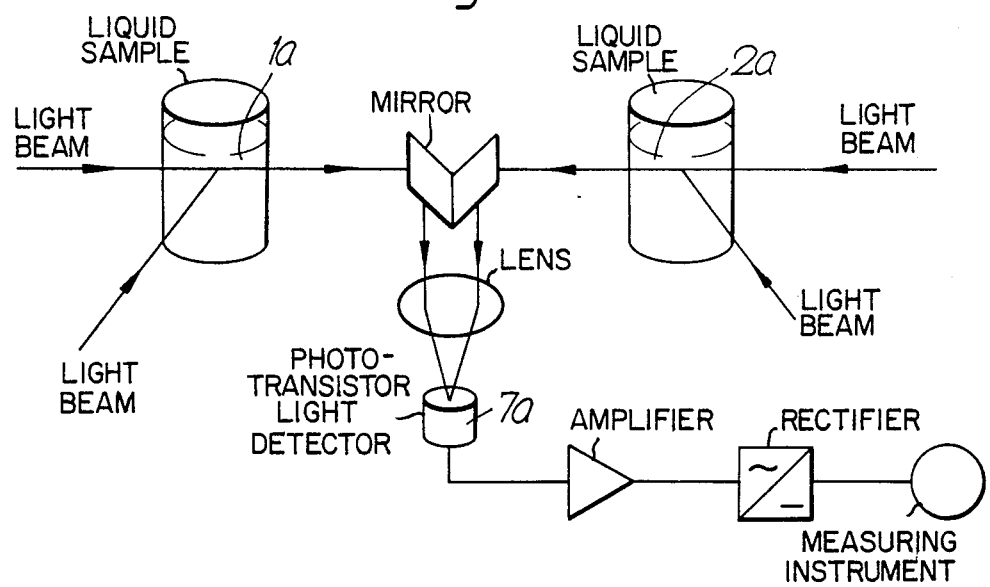

The invention comes out in more detail from the following description and from the attached drawings, wherein FIG. 1 illustrates an embodiment in which unevenness of the skin is measured on the occasion of local pimpledness of the skin in allergic reactions, and FIG. 2 illustrates an embodiment in which the difference in turbidness of two liquid samples is measured. As an example in the description of the method, a measurement of the difference in unevenness of two face samples is used. The way in which the nature of the samples affects the details of the performance of the method is obvious for a person skilled in the art. Likewise, it is obvious that this method can also be applied in the ultraviolet and infrared ranges.

In the method in accordance with the invention, two lights are used per sample, the angles between the directions of incidence and dispart of the said lights being different. The directing of the lights takes place in a way well known to a person skilled in the art, such as, e.g., by means of mirrors or prisms if one or two sources of light are used, or merely by means of positioning of the sources of light and of the lenses related to them, if any, if four sources of light are used. One of the face samples is called the face to be studied and the other one the reference face. Both of the faces are illuminated simultaneously, one of them with light of one direction and the other one with light of the other direction, and the lights reflected from both faces are allowed to act simultaneously upon one light detector. The directions of the lights are alternated with each other at an appropriate frequency, which frequency is selected, for example, within the range of 1 c/s to 10,000 c/s, so that both the electrical or mechanical control of the light direction and the light detector and the related electronics, such as amplifiers, are capable of operating at the frequency concerned reliably and precisely. Owing to the linearity of the light detector, the information on the difference between the reflection factors is retained, and if the unevenness of the faces is different, i.e. if the difference between the reflection factors of one face, with the two directions of light to be used, is different as compared with the corresponding difference in respect of the other face, the light detector yields an AC signal, whose frequency is the same as the frequency of alternation of the light directions and whose amplitude is proportional to the difference in unevenness between the faces. The result of the measurement is independent from the darkness of the sample, i.e. from its component neutral in respect of the direction of the absorption, and also independent from possible differences in colour between the samples.

It is evident for a person skilled in the art that, in general, in this method, the selection of the direction of the measurement light may also be performed after the sample, whereat the samples would be illuminated constantly by means of light of one direction.

Generally speaking, in the method in accordance with the invention, in order that the darkness of the sample should not affect the measurement result, it is necessary to adjust the intensity of the sources of light illuminating the same sample to such a level that lights of different directions produce an equally strong signal in the light detector. The adjusting takes place in practice so that a white calibration face is placed in the place of one of the samples and a black calibration face in the place of the other sample, and the intensity of light is adjusted either electrically or by means of filters so that the AC signal of the light detector becomes zero. The places of the black and the white calibration sample are reversed, and the adjustment operation is repeated.

In addition to the possibility that the samples may be different portions of the same face, they may also be, e.g., different portions of the same liquid or gas flow.

In the example of FIG. 1, the invention is applied to local pimpledness of the skin as a result of an allergic reaction. As sources of light 3 to 6, four light-emitting diodes of the same colour are used, of which two 3, 4 illuminate the skin perpendicularly and two 5, 6 obliquely. As the light detector, one phototransistor 7 is used, on which the light reflected from the two tests areas 1, 2 on the skin falls. The control unit 8 operates so that each test area is illuminated by one LED perpendicularly and one LED obliquely, so that always when one LED illuminates one test area perpendicularly, the other test area is illuminated by a LED obliquely. From FIG. 1 it will be seen that LED's 3 and 6 are energized in parallel, and LED's 4 and 5 are energized in parallel. The AC signal of the phototransistor 7 is passed to the amplifier 9, rectified, and measured.

The reflection factors of the test areas are denoted in perpendicular light with $D_1$ and $D_2$ and in oblique light with $S_1$ and $S_2$. When the sources of light alternate in the way described above, the AC signal of the light detector is proportional to the equation $$R=(D_1+S_2)-(D_2+S_1)$$

which is in a simple way obtained in the form $$R=(D_1-S_1)-(D_2-S_2)$$

The following denotations are used:

$$H_1=D_1-S_1$$

$$H_2=D_2-S_2$$

From this it follows:

$$R=H_1-H_2$$

The quantities $H_1$ and $H_2$ characterize the patterns of reflection directions of the samples. If the patterns of reflection directions of the samples are different, a signal is obtained which, since a difference between the patterns of reflection directions is a result of difference in unevenness, is the larger the greater the difference is in the unevenness of the faces.

In the application of FIG. 2, two liquid samples 1a and 2a are to be studied, and the property to be measured is the turbidness. Thus, the apparatus is a differential nephelometer. By means of methods in themselves known, the light is directed from one, two or four sources of light, in accordance with the figure, at the samples. Part of the light reaches the light detector 7a, in respect of whose AC signal the procedure is the same as was described above.

In general, in the method in accordance with the invention, when two or four sources of light are used, the balance adjustment can be performed automatically by means of a second light detector. To this second light detector, samples of both beams of light of different directions are passed alternatingly at an appropriate frequency, from one sample at a time, and the AC signal obtained is used for the adjustment of the ratio of the light intensities of the sources of light so that the AC signal concerned becomes zero. The DC signal of this second light detector can also be used for the stabilization of the light intensities of the sources of light.

The essential feature of the present invention is not what prior-art means are used for directing the beams of light at the sample or for selecting the direction of the light to be detected, departing from the sample, and for producing the alternation of the directions of light, whether it takes place by moving the optics belonging to the apparatus or by controlling the sources of light, or by displacing the samples, but all devices employing the said means are considered as included in the scope of protection of the invention.

What is claimed is:

1. Method for measuring the difference in response of two samples to incident light directed at the samples from different angles and detected by a common light detector, characterized by the steps of irradiating said two samples simultaneously during a first interval with a first pair of light beams, one beam of said first pair being directed at one of said samples at a first angle, the other beam of said first pair being directed at the other of said samples at a second angle different from said first angle, irradiating said two samples simultaneously during a second interval with a second pair of light beams, one beam of said second pair being directed at said second angle at said one of said samples, the other beam of said second pair being directed at said first angle at said other of said samples, said first and second intervals occurring alternately in succession, and detecting at a common point the light from said light beams reaching said common point due to a given optical parameter of said samples.

2. The method according to claim 1, characterized in that one of said light beam angles is normal to the surfaces of said samples.

3. The method according to claim 1, characterized in that said irradiation intervals are alternated at a frequency within the range of 1 c/s to 10,000 c/s.

* * * * *